US009415126B2

(12) United States Patent
Dobrinsky et al.

(10) Patent No.: US 9,415,126 B2
(45) Date of Patent: Aug. 16, 2016

(54) REFLECTIVE TRANSPARENT OPTICAL CHAMBER

(71) Applicant: Sensor Electronic Technology, Inc., Columbia, SC (US)

(72) Inventors: Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 14/285,869

(22) Filed: May 23, 2014

(65) Prior Publication Data

US 2014/0346370 A1 Nov. 27, 2014

Related U.S. Application Data

(60) Provisional application No. 61/826,784, filed on May 23, 2013.

(51) Int. Cl.
| | |
|---|---|
| *A61L 2/10* | (2006.01) |
| *C02F 1/32* | (2006.01) |
| *G01N 21/3504* | (2014.01) |
| *G01N 21/03* | (2006.01) |
| *G01N 21/33* | (2006.01) |
| *A61L 2/26* | (2006.01) |
| *G01N 21/31* | (2006.01) |

(52) U.S. Cl.
CPC ...... *A61L 2/10* (2013.01); *A61L 2/26* (2013.01); *C02F 1/325* (2013.01); *G01N 21/031* (2013.01); *G01N 21/0303* (2013.01); *G01N 21/33* (2013.01); *G01N 21/3504* (2013.01); *G01N 2021/317* (2013.01)

(58) Field of Classification Search
CPC ............. C02F 1/325; C02F 2201/3228; C02F 2201/3222; C02F 1/78; C02F 2201/326; C02F 1/001; C02F 1/32; C02F 2201/3224; C02F 2201/3225; C02F 2303/04; C02F 1/006; C02F 2301/026; C02F 2201/3223; A61L 2/10; A61L 9/20; A61L 2/183; A61L 2/202; F21Y 2103/00; F21V 13/04; G02B 6/0001; G02B 6/0096; G02B 27/0994; G02B 5/045; G02B 6/0055; G02B 6/0071; H01J 61/72
USPC .................................. 250/504 R, 428, 432 R
See application file for complete search history.

(56) References Cited

U.S. PATENT DOCUMENTS

| | | | | |
|---|---|---|---|---|
| 2,366,216 | A | * | 1/1945 | Roberts .......................... 362/256 |
| 3,867,665 | A | * | 2/1975 | Furmidge et al. .............. 313/485 |

(Continued)

FOREIGN PATENT DOCUMENTS

WO 9833056 A1 7/1998

*Primary Examiner* — Michael Logie
(74) *Attorney, Agent, or Firm* — LaBatt, LLC (57) ABSTRACT

A chamber configured to increase an intensity of target radiation emitted therein is provided. The chamber includes an enclosure at least partially formed by a set of transparent walls. Each transparent wall can comprise a first material transparent to the target radiation and having a refractive index greater than 1.1 for the target radiation. The outer surface of the set of transparent walls can include a set of cavities, each cavity comprising an approximately prismatic void. Additionally, a medium located adjacent to an outer surface of the set of transparent walls can have a refractive index within approximately one percent of a refractive index of a vacuum for the target radiation.

20 Claims, 11 Drawing Sheets

(56) References Cited

U.S. PATENT DOCUMENTS

| | | | | |
|---|---|---|---|---|
| 3,902,056 | A * | 8/1975 | Aizenberg | F21S 19/005 359/597 |
| 3,904,363 | A * | 9/1975 | Free | 250/431 |
| 4,140,487 | A * | 2/1979 | Garten et al. | 422/78 |
| 4,260,220 | A * | 4/1981 | Whitehead | G02B 6/0096 359/529 |
| 4,535,247 | A * | 8/1985 | Kurtz | 250/436 |
| 4,805,984 | A * | 2/1989 | Cobb, Jr. | 385/133 |
| 4,849,178 | A * | 7/1989 | Azuma | G01N 21/33 422/69 |
| 4,952,511 | A * | 8/1990 | Radmer | 435/292.1 |
| 4,963,750 | A * | 10/1990 | Wilson | 250/436 |
| 4,991,070 | A * | 2/1991 | Stob | 362/223 |
| 5,219,217 | A * | 6/1993 | Aikens | 362/560 |
| 5,395,522 | A * | 3/1995 | Melanson et al. | 210/202 |
| 5,481,637 | A * | 1/1996 | Whitehead | F21V 5/02 362/23.18 |
| 5,745,632 | A * | 4/1998 | Dreyer | G02B 6/032 359/831 |
| 6,280,060 | B1 | 8/2001 | Suzuki et al. | 362/294 |
| 6,337,946 | B1 | 1/2002 | McGaffigan | 385/146 |
| 6,543,912 | B1 * | 4/2003 | Simon | 362/327 |
| 7,300,499 | B1 | 11/2007 | Fleisher | |
| 7,777,955 | B2 * | 8/2010 | Cassarly et al. | 359/618 |
| 7,946,729 | B2 * | 5/2011 | Ivey | F21V 7/043 362/227 |
| 8,618,522 | B2 * | 12/2013 | McKinney | 250/504 R |
| 8,859,989 | B2 * | 10/2014 | From et al. | 250/435 |
| 9,320,818 | B2 * | 4/2016 | Vardiel | A61L 2/10 |
| 2003/0010927 | A1 * | 1/2003 | Wedekamp | 250/436 |
| 2003/0052278 | A1 * | 3/2003 | Duarte | 250/438 |
| 2003/0086848 | A1 * | 5/2003 | Saccomanno | A61L 2/10 422/292 |
| 2004/0091212 | A1 * | 5/2004 | Strecker | G01N 21/251 385/50 |
| 2004/0222163 | A1 * | 11/2004 | Saccomanno | 210/748 |
| 2004/0256582 | A1 * | 12/2004 | Laudano et al. | 250/504 R |
| 2006/0163169 | A1 * | 7/2006 | Eckhardt et al. | 210/748 |
| 2007/0024971 | A1 * | 2/2007 | Cassarly | G02B 6/0008 359/485.03 |
| 2008/0061005 | A1 * | 3/2008 | Hopaluk et al. | 210/748 |
| 2008/0305018 | A1 * | 12/2008 | Blum | 422/186.3 |
| 2009/0073682 | A1 * | 3/2009 | Yoon et al. | 362/224 |
| 2010/0074800 | A1 * | 3/2010 | Miwa et al. | 422/56 |
| 2010/0178201 | A1 * | 7/2010 | Tribelsky et al. | 422/24 |
| 2010/0209294 | A1 * | 8/2010 | Owen | A61L 9/205 422/24 |
| 2010/0237254 | A1 * | 9/2010 | Mason | A61L 2/10 250/435 |
| 2010/0258508 | A1 * | 10/2010 | Levy | 210/748.11 |
| 2010/0264329 | A1 * | 10/2010 | Vardiel | C02F 1/325 250/436 |
| 2010/0296971 | A1 | 11/2010 | Gaska et al. | |
| 2011/0234941 | A1 * | 9/2011 | Gourlay | 349/64 |
| 2011/0309032 | A1 * | 12/2011 | Makl | 210/748.1 |
| 2012/0153804 | A1 * | 6/2012 | Li | 313/485 |
| 2012/0228236 | A1 * | 9/2012 | Hawkins et al. | 210/748.14 |
| 2012/0298848 | A1 * | 11/2012 | Vasylyev | 250/227.11 |
| 2012/0312169 | A1 | 12/2012 | Chan et al. | |
| 2013/0048545 | A1 * | 2/2013 | Shatalov et al. | 210/96.1 |
| 2013/0270429 | A1 * | 10/2013 | Bilenko et al. | 250/252.1 |
| 2013/0270445 | A1 | 10/2013 | Gaska et al. | |
| 2014/0060096 | A1 | 3/2014 | Shur et al. | |
| 2014/0060104 | A1 | 3/2014 | Shur et al. | |
| 2014/0061509 | A1 | 3/2014 | Shur et al. | |
| 2014/0105784 | A1 * | 4/2014 | Smeeton et al. | 422/24 |
| 2014/0110351 | A1 * | 4/2014 | Fahs, II | 210/748.11 |
| 2015/0314024 | A1 * | 11/2015 | Khan | C02F 1/325 250/435 |

* cited by examiner

REFLECTIVE TRANSPARENT OPTICAL CHAMBER

REFERENCE TO RELATED APPLICATIONS

The current application claims the benefit of U.S. Provisional Application No. 61/826,784, titled "Reflective Transparent Chamber for Gas/Liquid Disinfection and Sensing," which was filed on 23 May 2013, and which is hereby incorporated by reference.

TECHNICAL FIELD

The disclosure relates generally to optical chambers, and more particularly, to an optical chamber having an increased intensity of light.

BACKGROUND ART

Optical gas detectors are well known. In particular, such detectors are used in the design of, for example, carbon dioxide and hydrocarbon gas detectors. In this case, infrared radiation emitted by a source can pass through a chamber containing the gas under test, where some of the infrared radiation will be absorbed by the gas. Absorption by a specific gas is a function of the wavelength of the infrared radiation. Therefore, by careful selection of an appropriate optical band-pass filter at a detector, it is possible to determine the presence of a specific gas. In addition to sensing carbon dioxide hydrocarbon gases, ozone detectors also use radiation. In this case, the radiation is in the ultraviolet range.

Air disinfection devices are available on the market and include air cleaners that filter airborne toxins, dust mites, and pet dander from the air. Some air purifiers can remove or reduce smoke, dust, and pollen from an environment, as well as reduce an amount of bacteria in the air. Unfortunately, reducing viral levels in the air is difficult with a conventional filter (such as a HEPA filter, for example), as viruses are not well captured by the filter due to their small size. Ultraviolet air disinfection devices have been utilized in the past for disinfecting air from viruses. Unfortunately, a problem with ultraviolet air purifiers is that they do not provide sufficient radiation levels in the air to get air well purified. For example, the ultraviolet light can get absorbed by the chamber walls containing disinfection gases, resulting in a relatively low efficiency of ultraviolet disinfection chambers. To date, the best reflective metallic material available for ultraviolet reflection constitutes well-polished aluminum, which is only 90% reflective. In order to increase an efficiency of such chambers, the chambers are required to be large in size making their usage difficult in a typical office environment.

In addition to air disinfection, ultraviolet emitters can be effectively used to disinfect liquids, such as water, and have found their use in various water treatment facilities. Water treatment using ultraviolet radiation offers many advantages over other forms of water treatment, such as chemical treatment. For example, treatment with ultraviolet radiation does not introduce additional chemical or biological contaminants into the water. Furthermore, ultraviolet radiation provides one of the most efficient approaches to water decontamination since there are no microorganisms known to be resistant to ultraviolet radiation, unlike other decontamination methods, such as chlorination. Ultraviolet radiation is known to be highly effective against bacteria, viruses, algae, molds, and yeasts. For example, hepatitis virus has been shown to survive for considerable periods of time in the presence of chlorine, but is readily eliminated by ultraviolet radiation treatment.

The removal efficiency of ultraviolet radiation for most microbiological contaminants, such as bacteria and viruses, generally exceeds 99%. To this extent, ultraviolet radiation is highly efficient at eliminating *E-coli, Salmonella*, Typhoid fever, Cholera, Tuberculosis, Influenza Virus, Polio Virus, and Hepatitis A Virus.

Ultraviolet radiation disinfection using mercury based lamps is a well-established technology. In general, a system for treating water using ultraviolet radiation is relatively easy to install and maintain in a plumbing or septic system. Use of ultraviolet radiation in such systems does not affect the overall system. However, it is often desirable to combine an ultraviolet purification system with another form of filtration since the ultraviolet radiation cannot neutralize chlorine, heavy metals, and other chemical contaminants that may be present in the water. Various membrane filters for sediment filtration, granular activated carbon filtering, reverse osmosis, and/or the like, can be used as a filtering device to reduce the presence of chemicals and other inorganic contaminants.

Mercury lamp-based ultraviolet radiation disinfection has several shortcomings when compared to deep ultraviolet (DUV) light emitting device (LED)-based technology, particularly with respect to certain disinfection applications. For example, in rural and/or off-grid locations, it is desirable for an ultraviolet purification system to have one or more of various attributes such as: a long operating lifetime, containing no hazardous components, not readily susceptible to damage, requiring minimal operational skills, not requiring special disposal procedures, capable of operating on local intermittent electrical power, and/or the like. Use of a DUV LED-based solution can improve one or more of these attributes as compared to a mercury vapor lamp-based approach. For example, in comparison to mercury vapor lamps, DUV LEDs: have substantially longer operating lifetimes (e.g., by a factor of ten); do not include hazardous components (e.g., mercury), which require special disposal and maintenance; are more durable in transit and handling (e.g., no filaments or glass); have a faster startup time; have a lower operational voltage; are less sensitive to power supply intermittency; are more compact and portable; can be used in moving devices; can be powered by photovoltaic (PV) technology, which can be installed in rural locations having no continuous access to electricity and having scarce resources of clean water; and/or the like.

SUMMARY OF THE INVENTION

Aspects of the invention provide a chamber configured to increase an intensity of target radiation emitted therein. The chamber includes an enclosure at least partially formed by a set of transparent walls. Each transparent wall can comprise a first material transparent to the target radiation and having a refractive index greater than 1.1 for the target radiation. The outer surface of the set of transparent walls can include a set of cavities, each cavity comprising an approximately prismatic void. Additionally, a medium located adjacent to an outer surface of the set of transparent walls can have a refractive index within approximately one percent of a refractive index of a vacuum for the target radiation.

A first aspect of the invention provides a chamber comprising: an enclosure at least partially formed by a set of transparent walls having outer and inner surfaces, wherein each transparent wall comprises a first material transparent to target radiation and having a refractive index greater than 1.1 for the target radiation, wherein a medium located adjacent to the outer surface of the set of transparent walls has a refractive index within approximately one percent of a refractive index of a vacuum for the target radiation, and wherein the outer surface of the set of transparent walls includes a set of cavities, each cavity comprising an approximately prismatic void.

A second aspect of the invention provides a system comprising: an enclosure having an inlet for receiving a fluid, wherein the enclosure is at least partially formed by a set of transparent walls having outer and inner surfaces, wherein each transparent wall comprises a first material transparent to target radiation and having a refractive index greater than 1.1 for the target radiation, wherein a medium located adjacent to the outer surface of the set of transparent walls has a refractive index within approximately one percent of a refractive index of a vacuum for the target radiation, and wherein the outer surface of the set of transparent walls includes a set of cavities, each cavity comprising an approximately prismatic void; and a light source located within the enclosure, wherein the light source is configured to emit the target radiation within the enclosure while the fluid is present in the enclosure.

A third aspect of the invention provides a system comprising: an enclosure having an inlet for receiving a fluid, wherein the enclosure is at least partially formed by a set of transparent walls having outer and inner surfaces, wherein each transparent wall comprises one of: sapphire or fused silica, wherein a medium located adjacent to the outer surface of the set of transparent walls has a refractive index within approximately one percent of a refractive index of a vacuum for ultraviolet radiation, and wherein the outer surface of the set of transparent walls includes a set of cavities, each cavity comprising an approximately prismatic void; and a light source located within the enclosure, wherein the light source is configured to emit the ultraviolet radiation within the enclosure while the fluid is present in the enclosure.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a chamber configured to increase an intensity of target radiation emitted therein. The chamber includes an enclosure at least partially formed by a set of transparent walls. Each transparent wall can comprise a first material transparent to the target radiation and having a refractive index greater than 1.1 for the target radiation. The outer surface of the set of transparent walls can include a set of cavities, each cavity comprising an approximately prismatic void. Additionally, a medium located adjacent to an outer surface of the set of transparent walls can have a refractive index within approximately one percent of a refractive index of a vacuum for the target radiation.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately ten nanometers (nm) to approximately four hundred nm, while ultraviolet-C (UV-C) means electromagnetic radiation having a wavelength ranging from approximately one hundred nm to approximately two hundred eighty nm, ultraviolet-B (UV-B) means electromagnetic radiation having a wavelength ranging from approximately two hundred eighty to approximately three hundred fifteen nanometers, and ultraviolet-A (UV-A) means electromagnetic radiation having a wavelength ranging from approximately three hundred fifteen to approximately four hundred nanometers. As also used herein, a material/structure is considered to be "reflective" to radiation of a particular wavelength when the material/structure has a reflectivity of at least thirty percent for radiation of the particular wavelength radiated normally to the surface of the material/structure. In a more particular embodiment, a highly reflective material/structure has a reflectivity of at least seventy percent for radiation of the particular wavelength radiated normally to the surface of the material/structure. Furthermore, a material/structure is considered to be "transparent" to radiation of a particular wavelength when the material/structure allows a significant amount of the radiation to pass there through (e.g., at least ten percent of the radiation radiated at a normal incidence to an interface of the material/structure).

As used herein, the term "disinfection" and its related terms means treating a medium so that the medium includes a sufficiently low number of contaminants (e.g., chemical) and microorganisms (e.g., virus, bacteria, and/or the like) so that the medium can be utilized as part of a desired human interaction with no or no reasonable risk for the transmission of a disease or other harm to the human. For example, disinfection of the medium means that the medium has a sufficiently low level of active microorganisms and/or concentration of other contaminants that a typical human can interact with the medium without suffering adverse effects from the microorganisms and/or contaminants present on or in the medium. In addition, disinfection can include sterilization. As used herein, the term "sterilization" and its related terms means neutralizing an ability of a microorganism to reproduce, which may be accomplished without physically destroying the microorganism. In this example, a level of microorganisms present on the item cannot increase to a dangerous level and will eventually be reduced, since the replication ability has been neutralized. A target level of microorganisms and/or contaminants can be defined, for example, by a standards setting organization, such as a governmental organization.

Figure 1A:
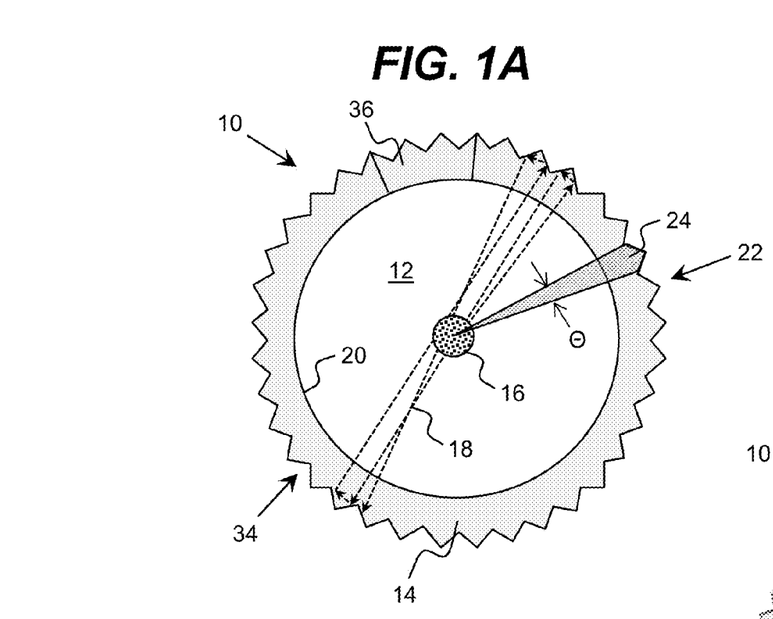
FIGS. 1A and 1B show front and perspective views, respectively, of an illustrative chamber according to an embodiment.
Figure 1B:
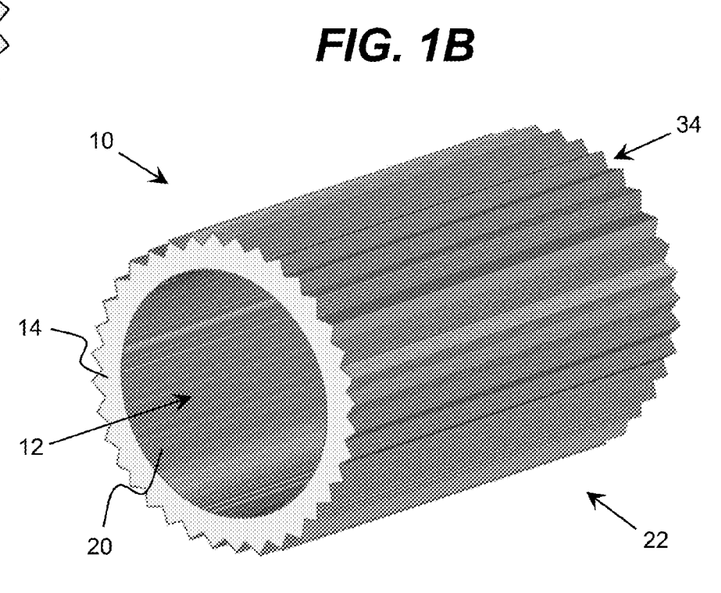

Turning to the drawings, FIGS. 1A and 1B show front and perspective views, respectively, of an illustrative chamber 10 according to an embodiment. The chamber 10 includes an enclosure 12 at least partially formed by one or more walls 14 having an inner surface 20 and an outer surface 22. The walls 14 can be formed of a material transparent to target radiation (e.g., radiation having a wavelength within a target range of wavelengths). In an embodiment, the material comprises a high refractive index (also referred to as index of refraction), e.g., greater than approximately 1.1, for the target radiation. In a more particular embodiment, the refractive index is greater than approximately 1.45 for the target radiation. When the target radiation is ultraviolet radiation, the walls 14 can be formed of sapphire, which has a refractive index of approximately 1.8. Additionally, fused silica has a refractive index of approximately 1.49 for ultraviolet light. In an embodiment, a total internal reflection angle for the target radiation is greater than forty-five degrees.

It is understood that each chamber described herein will include an inlet and an outlet to enable a fluid, such as a gas or liquid, to enter and exit the chamber. When the chamber 10 includes one or more enclosed ends, such as one or more ends of the cylinder, the end can be formed of a reflective material. In an embodiment, the end can be formed of a material highly reflective of radiation having a target wavelength, such as a metal.

Additionally, the chamber 10 includes a light source 16 located within the enclosure 12. The light source 16 can be configured to emit radiation 18 having predominant wavelength(s) within the target range of wavelengths. The light source 16 can comprise any type of light source 16 including, for example, one or more light emitting diodes (LEDs), a mercury lamp, one or more light guiding structures (e.g., optical fibers), and/or the like. The target range of wavelengths can be within any range including, for example, visible, infrared, and/or the like. In an embodiment, the target range of wavelengths is within the ultraviolet range of wavelengths. In a more specific embodiment, the target range of wavelengths is between approximately 230 nanometers and approximately 360 nanometers, e.g., when the chamber 10 is utilized for disinfection of biological contaminants. To this extent, the target radiation can comprise a peak radiation that is substantially the same as (e.g., the full width at half maximum of one hundred nanometers or less) a wavelength used for purification of the corresponding fluid (e.g., a liquid such as water). The light source 16 can be centrally located within the enclosure 12. In an embodiment, a radius of the enclosure 12 is significantly larger than a radius of the light source 16. For example, the radius of the enclosure 12 can be at least ten times the radius of the light source 16. In an illustrative embodiment, the radius of the enclosure 12 is approximately forty-eight times the radius of the light source 16.

A material for forming the set of walls 14 can be selected based on the radiation emitted by the light source and a target refractive index for the set of walls 14. For example, when the radiation comprises ultraviolet radiation, the set of walls 14 can be formed of sapphire, fused silica, and/or the like. In an embodiment, a medium adjacent to the outer surface 22 of the set of walls 14 has a low refractive index. In a more particular embodiment, the refractive index of the medium is within approximately one percent of a refractive index of a vacuum for radiation having a wavelength within the target range of wavelengths. In a still more particular embodiment, the medium adjacent to the outer surface 22 of the set of walls 14 (e.g., surrounding the chamber 10) is atmospheric air, a vacuum, a gas, and/or the like.

Figure 2:
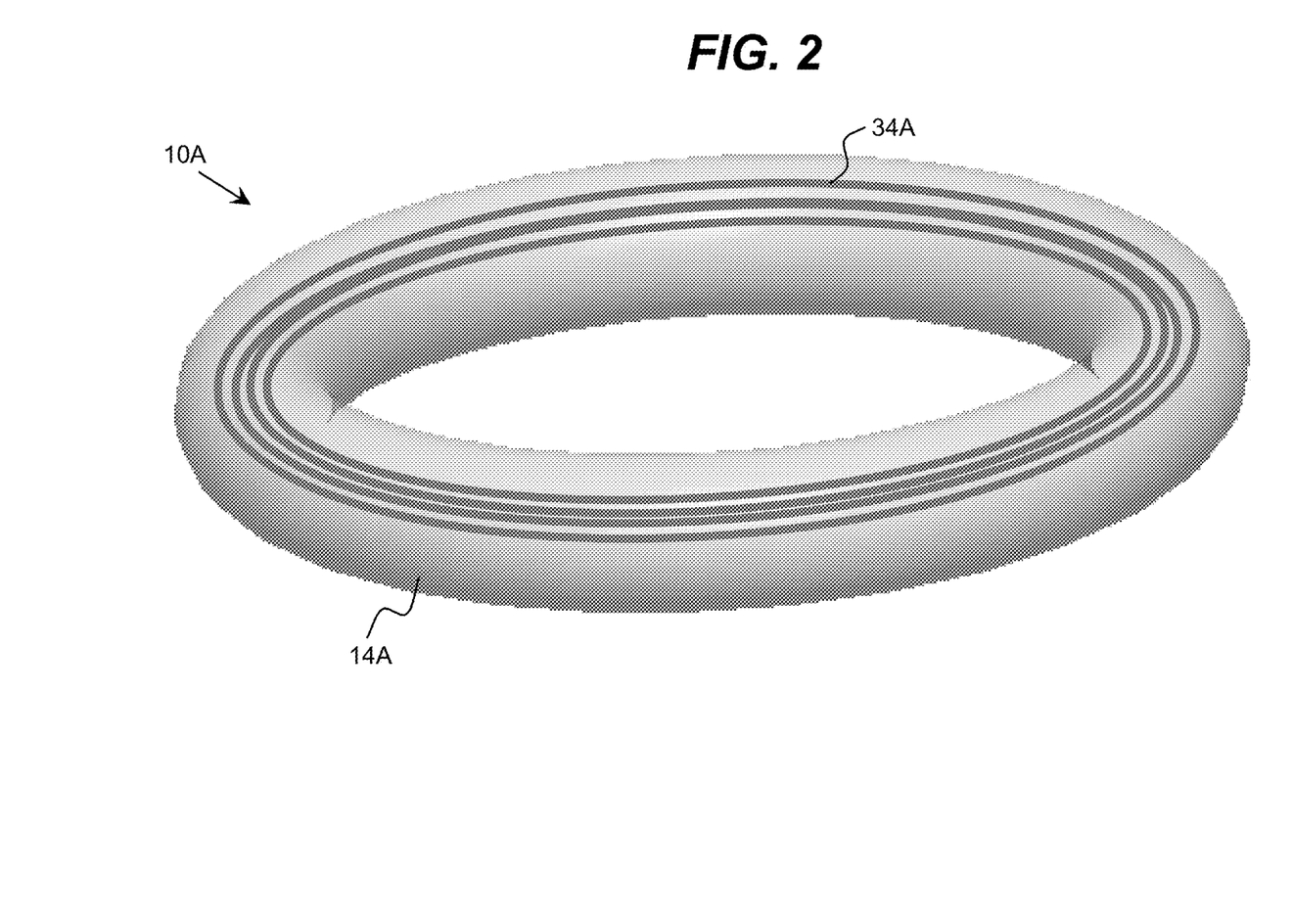
FIG. 2 shows an illustrative chamber comprising a wall in the shape of a torus according to an embodiment.

As illustrated, at least a portion of the enclosure 12 can be defined by a cylindrical wall 14. More generally, the wall 14 can be referred to as a body of revolution. In particular, a body of revolution comprises a shape that can be formed by symmetrically duplicating a section of the shape along a circular arc. For example, the segment 24 of the wall 14, which is defined by an angle Θ=10°, can be symmetrically repeated thirty-six times to create the wall 14 forming the enclosure 12. It is understood that a cylinder is only illustrative of various bodies of revolution including, for example, cones, truncated cones, tori, and/or the like. To this extent, FIG. 2 shows an illustrative chamber 10A comprising a wall 14A in the shape of a torus according to an embodiment. In this case, the revolution line is a line in the center of the torus. In each case, the body of revolution can have any of various radiuses along an axis of the body of revolution (e.g., cylinder or torus axis). Furthermore, it is understood that a segment 24 defined by an angle Θ of 10° is only illustrative, and the walls 14 can be formed of any number of segments symmetrically repeated any number of times.

In general, chambers formed using segments 24 defined by a smaller angle θ will provide better performance as the enclosure 12 becomes a closer approximation of a circular arc. However, even chambers formed using segments 24 defined by large angles, such as an angle Θ of 45°, can result in noticeable improvement as compared to chambers having walls without grooves. It is understood that the term "body of revolution" primarily refers to the internal circular shape of the enclosure 12 as defined by the inner surface 20. A distance from the center of the enclosure 12 to the inner surface 20 is referred to herein as the radius of the enclosure 12, whereas a distance from the center of the enclosure 12 to the outermost point of the walls 14 is referred to as the radius of the chamber 10A.

Figure 3A:
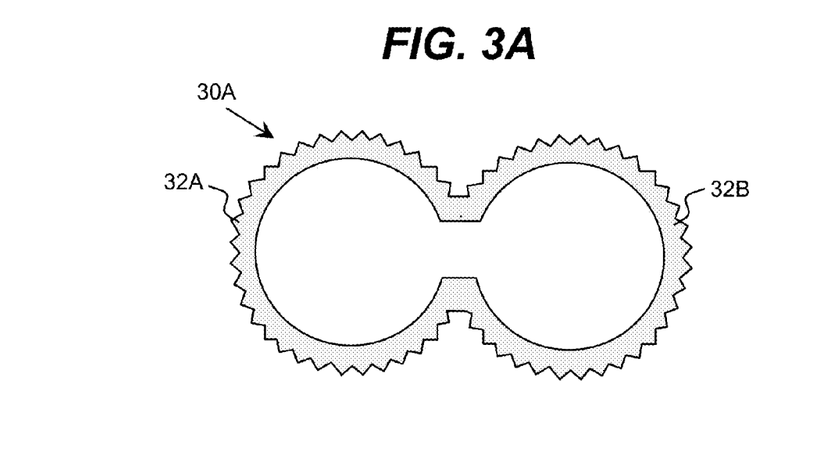
FIGS. 3A and 3B show cross sections of illustrative chambers according to other embodiments.
Figure 3B:
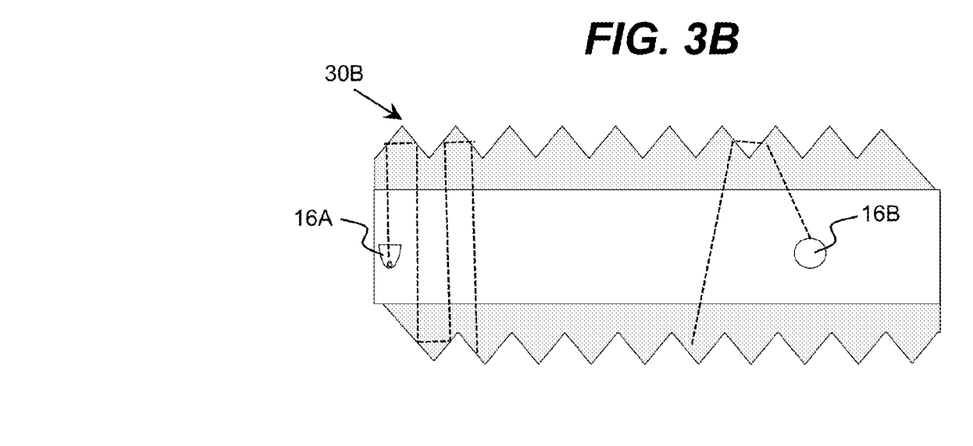

Furthermore, it is understood that a body of revolution is only illustrative of various chamber shapes, including non-revolution based chambers. For example, FIGS. 3A and 3B show cross sections of illustrative chambers 30A, 30B, respectively, according to other embodiments. In FIG. 3A, the chamber 30A has a shape formed by a combination of multiple revolution-like sub-chambers 32A, 32B. In FIG. 3B, the chamber 30B has a rectangular shape. When the rectangular shape is utilized, a collimated light source 16A and/or a Lambertian or uniform light source 16B can be utilized to generate radiation having a target wavelength.

Returning to FIG. 1A, as described herein, an outer surface 22 of one or more walls 14 of the chamber 10 includes a plurality of cavities 34 (e.g., voids or grooves). As illustrated, the cavities 34 can be configured to trap light rays 18 emitted by the light source 16 by total internal reflection. In an embodiment, the cavities 34 have an approximately prismatic shape. In a more particular embodiment, the prismatic shape of the cavities 34 comprises a triangular prism (as shown in FIG. 1B). For the torus-shaped chamber 10A shown in FIG. 2, the cavities 34A can comprise grooves formed around the outer surface of the walls 14A.

Figure 4:
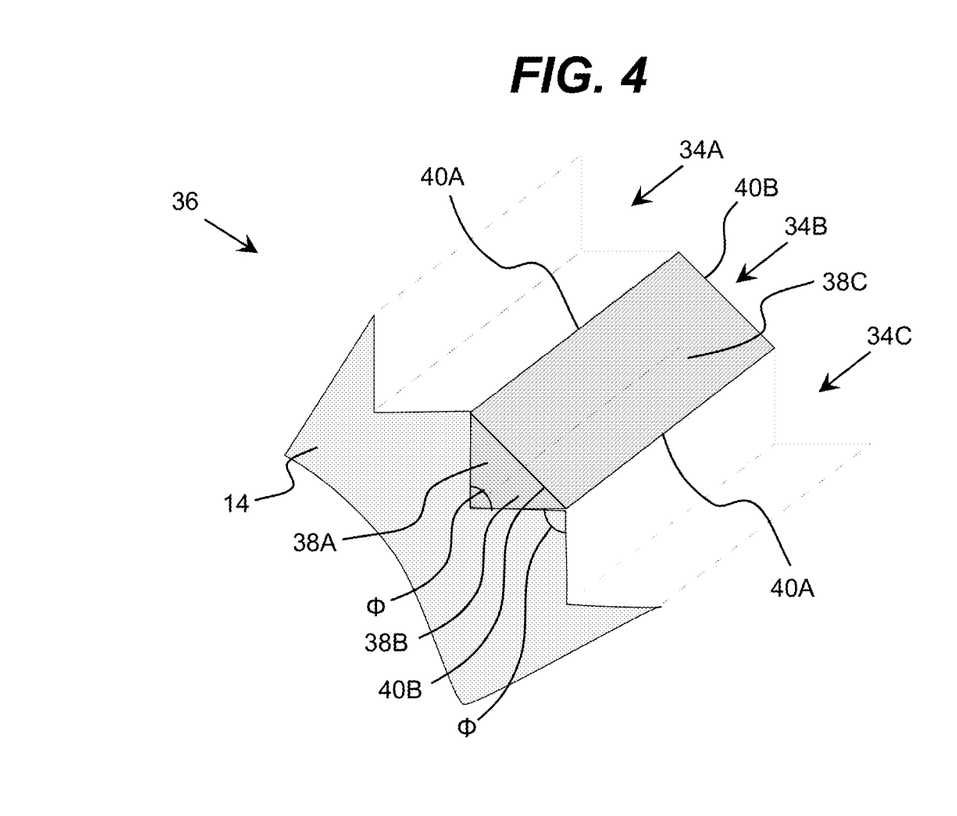
FIG. 4 shows an enlarged view of a portion of the wall shown in FIGS. 1A and 1B according to an embodiment.

FIG. 4 shows an enlarged view of a portion 36 of the wall 14 according to an embodiment. As illustrated, the portion 36 includes three cavities 34A, 34B, 34C. As shown in conjunction with cavity 34B, each cavity 34A-34C comprises a triangular prism having a pair of rectangular elongated sides 38A, 38B defined by intersecting external surfaces of the wall 14. The intersection of the elongated sides 38A, 38B can form any angle φ, which can be selected based on a refractive index of the wall 14. In an embodiment, the elongated sides 38A, 38B are substantially orthogonal to each other (e.g., form an angle φ of approximately ninety degrees) when the refractive index is approximately 1.42 or higher. For material having a lower refractive index, a more complicated structure may be utilized as described herein. Regardless, the angle φ can be selected to provide a first reflection of a ray at an interface between the wall 14 and a medium surrounding the chamber in a direction substantially perpendicular to the radius of the enclosure. In an embodiment, the angle φ is selected such that an angle between the corresponding normal directions for the elongated sides 38A, 38B is the larger of twice the total internal reflection angle or ninety degrees. In another embodiment, a length of a short side of each of the elongated sides 38A, 38B (e.g., corresponding to a depth of the external surfaces of the wall 14) are substantially equal.

Furthermore, the cavity 34B includes an elongated face 38C formed by the long edges 40A of each side 38A, 38B and short edges 40B located at opposing ends of the elongated sides 38A, 38B. To this extent, the long edges 40A can be as long as a length of the chamber 10 (FIG. 1B). However, the short edges 40B can have a length that is a small fraction of a radius of the enclosure 12 (FIG. 1A). In an embodiment, a length of each of the short edges 40B (e.g., a depth of each of the sides 38A, 38B) are substantially equal. In another embodiment, a length of the short edges 40B can be approximately one sixth of the radius of the enclosure 12 and the wall 14 includes thirty-six cavities 34A-34C having a triangular prism shapes formed around a circumference of the wall 14. However, it is understood that these are only illustrative, and embodiment can include different amounts of cavities, cavities of different shapes, and/or the like. In an embodiment, the wall 14 includes at least six cavities. However, inclusion of a large number of cavities 34A-34C can improve the reflective properties of the wall 14.

Figure 5A:
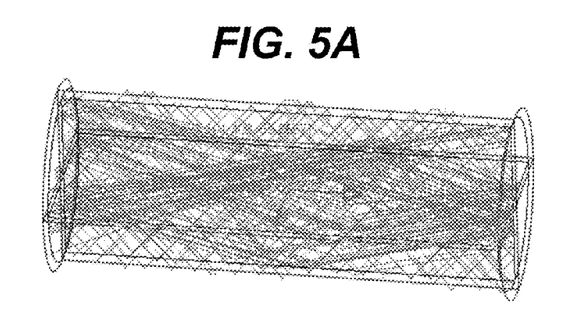
FIGS. 5A-5C show results of ray tracing simulations according to an embodiment.
Figure 5B:
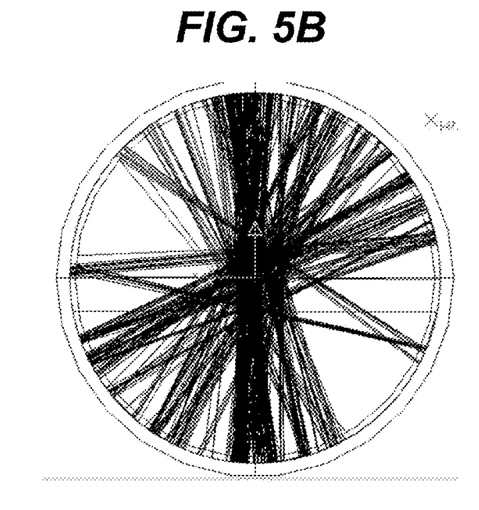
Figure 5C:
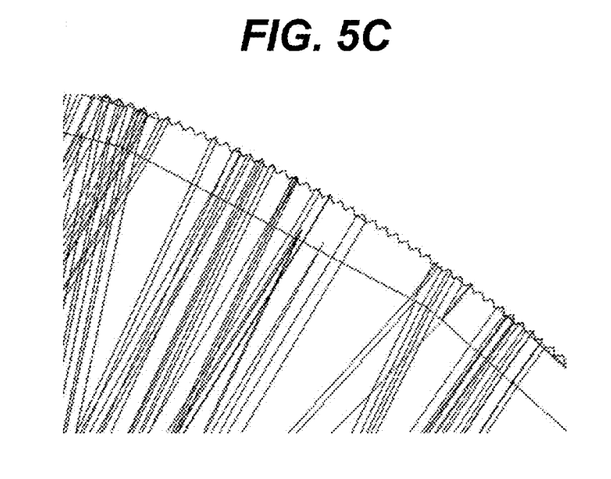

Ray tracing simulations were performed for a chamber 10 comprising a cylindrical enclosure 12 having a radius forty-eight times a radius of a centrally located light source 16. The walls 14 in the simulation include seven hundred twenty cavities 34, which corresponds to an angle Σ=0.5°, each having a triangular prism shape. In the simulation a refractive index of the walls 14 was assumed to be 1.82 (e.g., corresponding to sapphire) and the ends of the enclosure 12 were modeled as including ninety percent reflective material (mirrors). FIGS. 5A-5C show results of the ray tracing simulations according to an embodiment, illustrating the trapped rays within the chamber. As illustrated by the close up view of FIG. 5C, the random rays are totally internally reflected by the prismatic elements on the outer chamber surface due to a radial component of the emitted light. As shown in FIG. 5A, light rays having a component along the direction of the chamber are still totally internally reflected. FIG. 5B shows a trajectory of a single ray radiated from a center of the chamber. As illustrated, the ray follows a complex trajectory, but is well trapped by the chamber walls due to total internal reflection. When the enclosure has a rectangular shape as shown in FIG. 3B, interaction of multiple groove-like elements can promote recirculation of the light in the enclosure.

Figure 6:
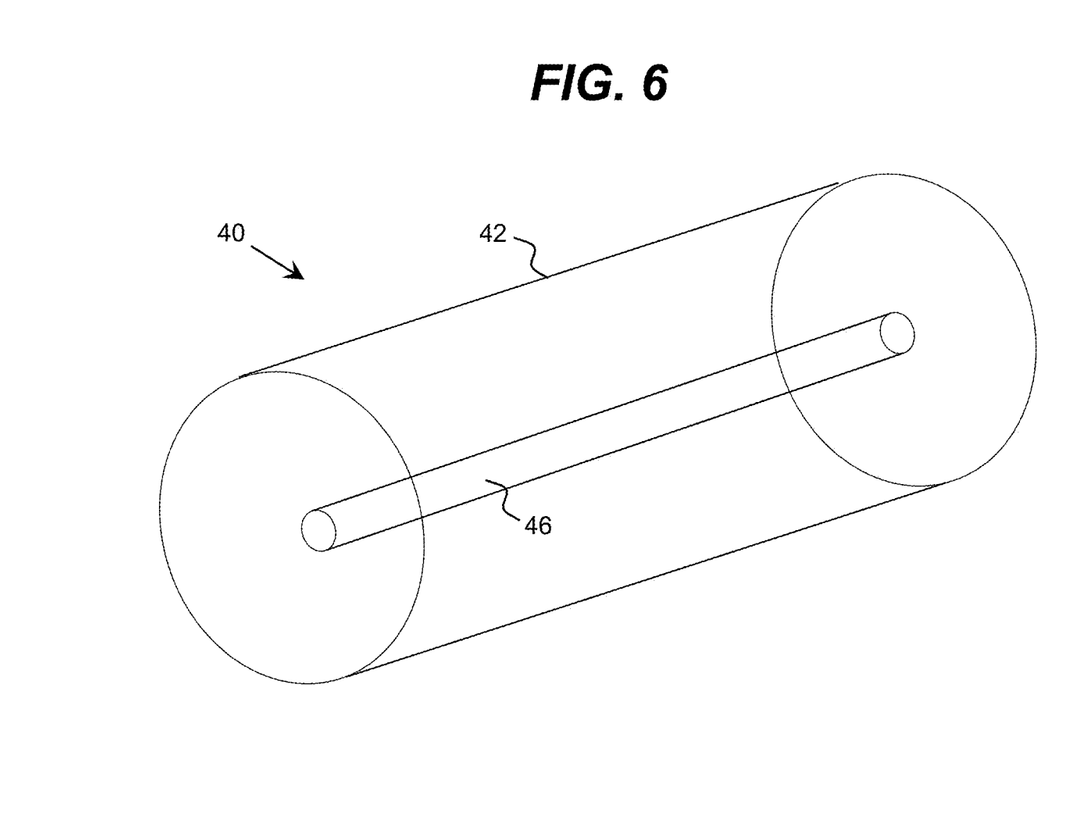
FIG. 6 shows a schematic of an illustrative chamber according to an embodiment.

Returning to FIGS. 1A and 1B, any combination of one or more of various types of light sources 16 can be utilized to generate radiation within the enclosure 12. In an embodiment, the light source 16 comprises a body of revolution. To this extent, FIG. 6 shows a schematic of an illustrative chamber 40 according to an embodiment. The chamber 40 includes a cylindrical enclosure 42 (e.g., defined by the inner surface of walls of the chamber 40) and a cylindrical light source 46 centrally located along a length of the enclosure 42. The light source 46 can comprise any type of light source. For example, the light source 46 can comprise a mercury lamp in a form of a long cylinder. Similarly, for the torus-shaped chamber 10A shown in FIG. 2, the light source can comprise a bent mercury lamp located along a central portion of the interior of the wall 14A. In an embodiment, the mercury lamp emits ultraviolet light. A benefit of using such a lamp is its transparency to ultraviolet light, which will both exit and enter the lamp while entrapped within the enclosure 12 as described herein.

Figures 7A, 7B:
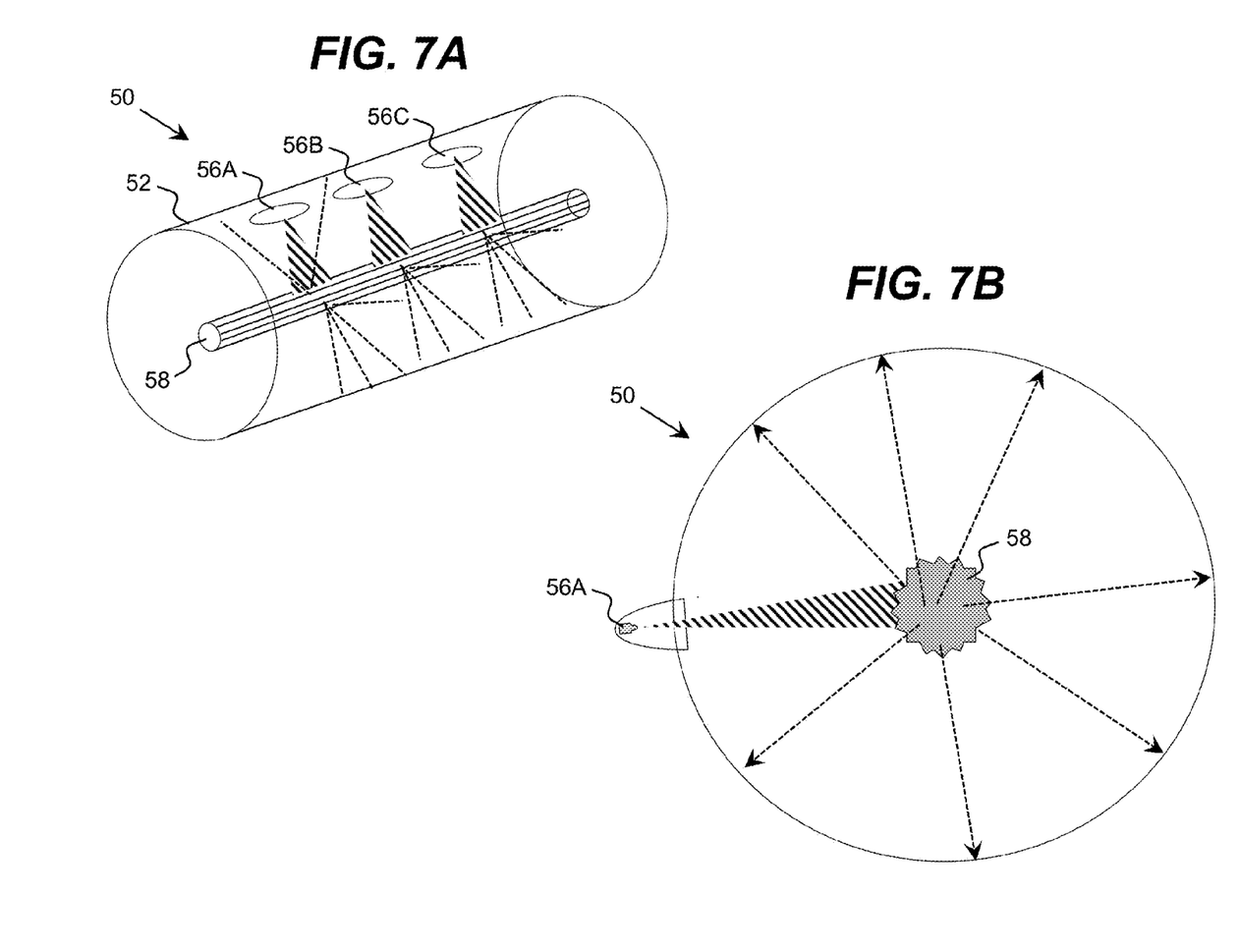
FIGS. 7A and 7B show perspective and cross-section views, respectively, of an illustrative chamber according to an embodiment.

In another embodiment, light source(s) can be located outside of the central portion of the enclosure. For example, FIGS. 7A and 7B show perspective and cross-section views, respectively, of an illustrative chamber 50 according to an embodiment. In this case, the chamber 50 includes multiple light sources 56A-56C located along the edge of the enclosure 52 (e.g., embedded in a wall forming the enclosure 52). While three light sources 56A-56C are shown, it is understood that any number of light sources in any arrangement can be utilized. The light sources 56A-56C can comprise any combination of one or more of various types of light sources. In an embodiment, the light sources 56A-56C comprise light emitting diodes, such as ultraviolet light emitting diodes.

Furthermore, the chamber 50 can include a light scattering center 58 located along a central axis of the enclosure 52. The light sources 56A-56C can be configured to emit light directed towards the light scattering center 58. For example, as shown in FIG. 7B, a light source 56A can be configured to emit collimated or partially collimated radiation to focus the light on the scattering center 58. For example, the light source 56A can include a light emitter and a reflector, such as a parabolic reflector, a conic reflector, and/or the like, which collimates or partially collimates light emitted by the light emitter and directs the light toward the scattering center 58. The light scattering center 58 can be formed using any solution. For example, the light scattering center 58 can comprise a polytetrafluoroethylene (e.g., Teflon) film, a sapphire rod with roughened surfaces, and/or the like.

Figure 8A:
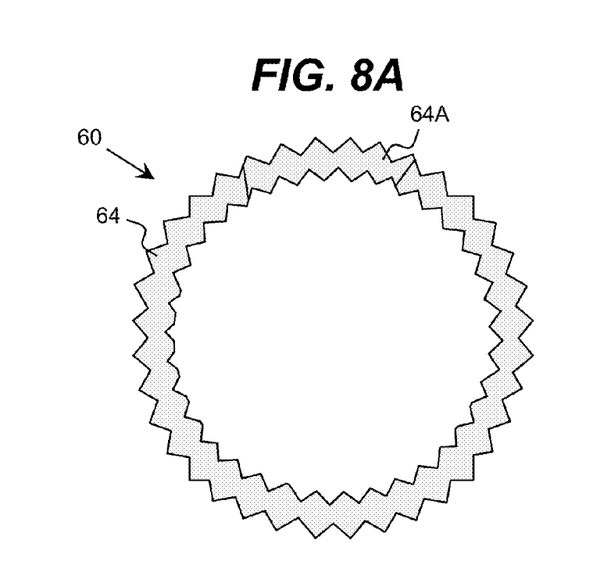
FIGS. 8A and 8B show a cross-section and an enlarged view of a portion of the cross-section of an illustrative chamber according to an embodiment.
Figure 8B:
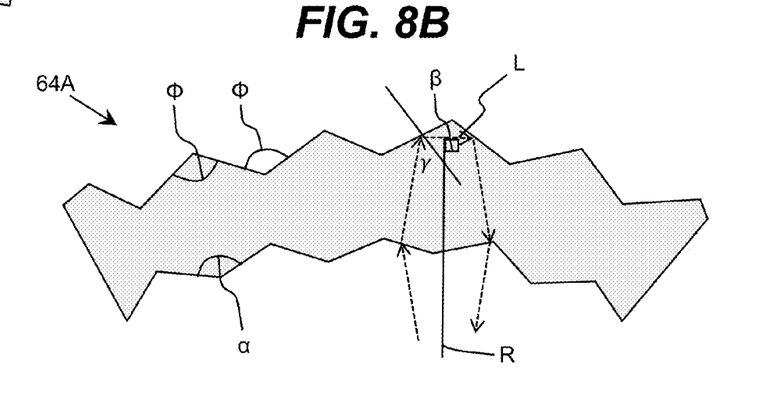

It is understood that a chamber described herein can include one or more additional features to increase light intensity within the corresponding enclosure. For example, an inner surface of one or more of the wall(s) can be configured to prevent radiation from escaping the enclosure. To this extent, FIGS. 8A and 8B show a cross-section and an enlarged view of a portion 64A of the cross-section of an illustrative chamber 60 according to an embodiment. In this case, both the inner and outer surfaces of the wall 64 have cavities formed therein. This configuration for the wall 64 can be utilized, for example, when the wall 64 is formed of a material having a low refractive index, e.g., below 1.45. In an embodiment, the angle φ and the angle α can be configured to improve the total internal reflectance of the enclosure. For example, the angles φ and α can be selected such that the angle γ is larger than the total internal reflection angle and the angle β, which corresponds to an angle formed between an intersection of the reflected ray L and a radius of the enclosure R at the midpoint of the ray L, is substantially equal to ninety degrees. In an embodiment, the cavities on the inner surface are aligned to substantially match the cavities on the outer surface as shown.

Figure 9:
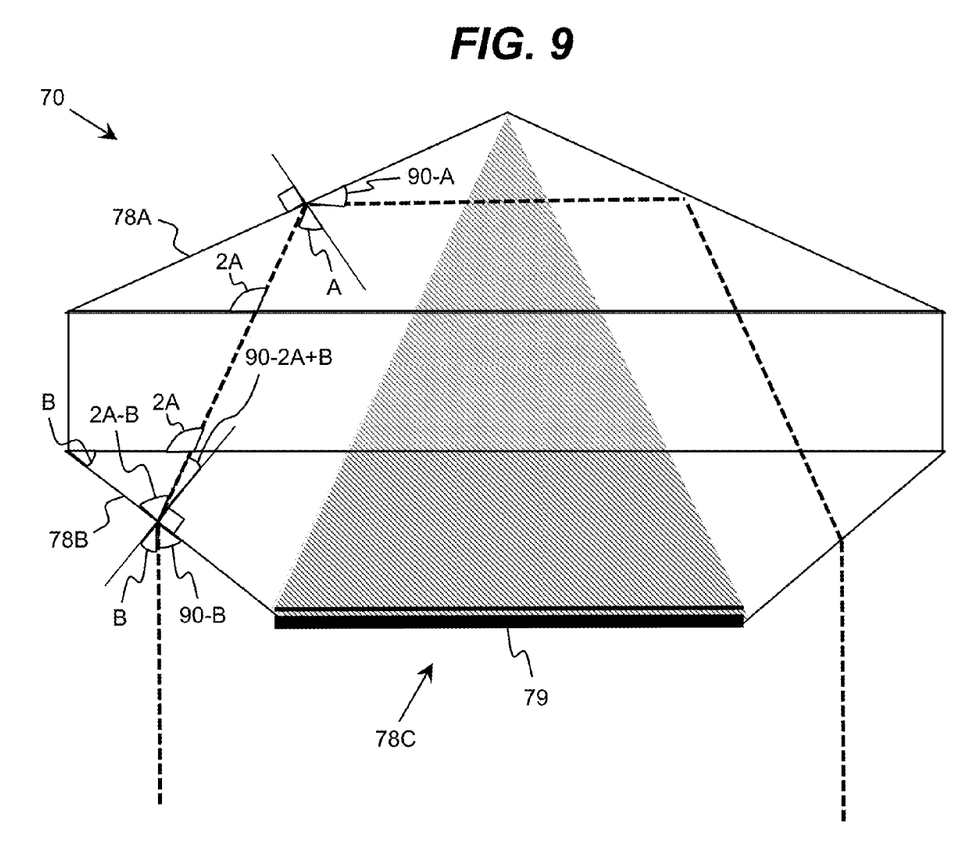
FIG. 9 shows a diagram of an illustrative portion of a wall configured to increase reflection according to an embodiment.

FIG. 9 shows a diagram of an illustrative portion of a wall 70 configured to increase reflection according to an embodiment. For example, a ray impinging a side 78A at an angle A to the side normal undergoes refraction at a side 78B. The refraction at side 78B can be calculated as: $n_1 \sin(B) = n_2 \sin(90-2A+B)$. The angle B can be determined by simplifying this equation to: $\operatorname{ctg}(B) = n_1/(n_2 \cos(2A)) - 1$, for each A, provided that the angle A is greater than the angle of total internal reflection from the side 78A. Furthermore, the angle A can be related to the angle φ described herein. In this embodiment, rays entering the shaded region of the wall 70 will not experience total internal reflection. As a result, an embodiment provides the side 78C with a coating of a reflective material 79, such as a reflective metallic layer. In this case, the wall 70 uses both total internal reflection and reflection from reflective material(s) 79 to increase the light intensity within the corresponding enclosure.

Figure 10:
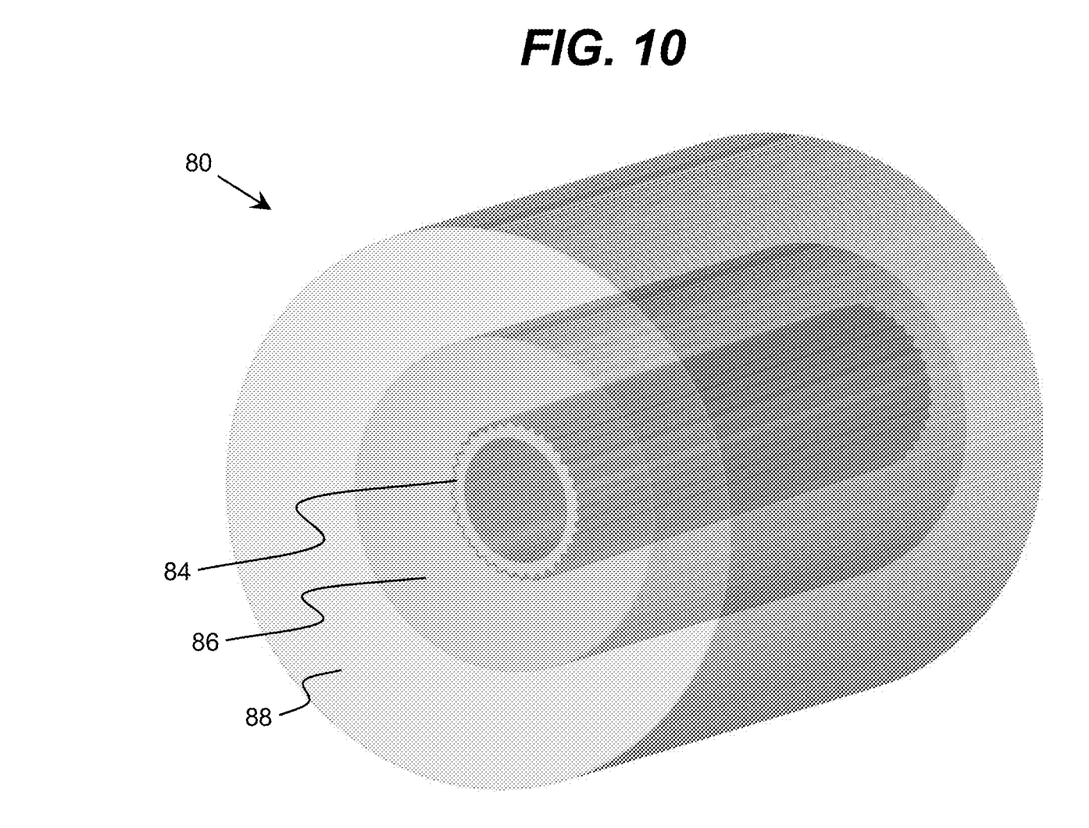
FIG. 10 shows a perspective view of an illustrative chamber according to an embodiment.

Furthermore, a chamber described herein can include one or more features external to the walls and enclosure to increase a light intensity within the enclosure. For example, FIG. 10 shows a perspective view of an illustrative chamber 80 according to an embodiment. In this case, the chamber 80 includes a wall 84 forming a cylindrical enclosure. The wall 84 can be configured to increase light intensity within the enclosure using a solution described herein. The chamber 80 further includes a reflective container 86, which encloses the wall 84. The reflective container 86 can be formed of a highly reflective material, such as highly polished aluminum or the like. The reflective container 86 can be spaced from the wall 84 to allow a medium having a refractive index substantially equal to one to be immediately adjacent to the wall 84.

The chamber 80 also is shown including an absorbing container 88 configured to prevent any radiation from escaping the chamber 80. The absorbing container 88 can have a sufficient thickness and be formed of any material capable of absorbing all of the radiation, which may escape through the wall 84 and/or reflective container 86. Illustrative materials include plastic, glass, metal, such as aluminum or steel, and/or the like. It is understood that the chamber 80 is only illustrative. To this extent, in other embodiments, the enclosure can have a different shape, the reflective container 86 or absorbing container 88 may not be included, and/or the like.

A chamber described herein can be utilized in any of various applications. For example, the chamber can be utilized in a system for disinfecting a fluid, such as water, air, and/or the like. Furthermore, the chamber can be utilized in a system for detecting a presence of and/or level of a substance in a fluid, such as a contaminant, a gas, and/or the like. In an illustrative embodiment, the chamber is utilized for detecting a concentration of ozone in a gas. In either case, the system can introduce the fluid into the chamber through an inlet included therein and the fluid can exit the chamber through an outlet. When desired, a filter can be located prior to the inlet to remove at least some contaminants from the fluid. Additionally, the system can include a component for determining a transparency of the fluid (e.g., a light source and light sensor, such as a photodiode, placed at an inlet of the enclosure), which can provide feedback to enable the system to adjust radiation levels and/or flow rate within the enclosure.

Figure 11:
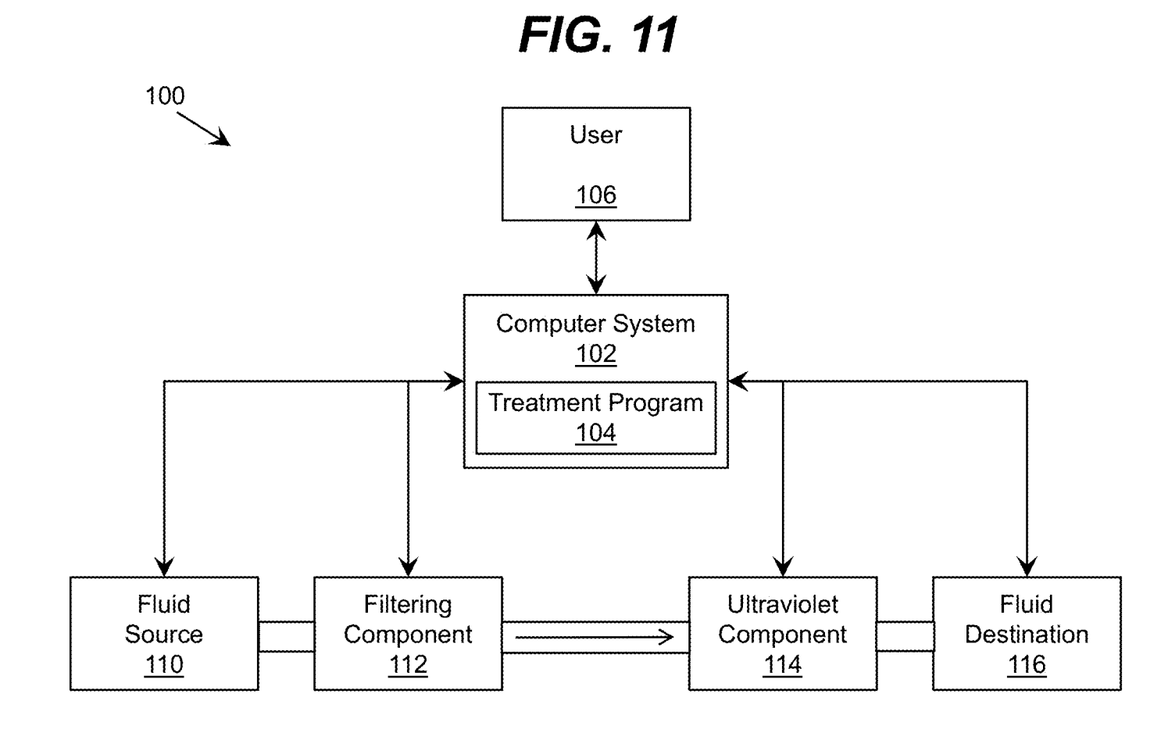
FIG. 11 shows an illustrative system for treating a fluid according to an embodiment.

FIG. 11 shows an illustrative system 100 for treating a fluid according to an embodiment, which can utilize a chamber described herein. In particular, the system 100 includes a computer system 102, which can perform a process described herein in order to treat the fluid as it travels from a fluid source 110 to a fluid destination 116. In particular, the computer system 102 is shown including a treatment program 104, which makes the computer system 102 operable to treat the fluid by performing a process described herein.

In an embodiment, the computer system 102 comprises a general purpose computing device, which includes a processor, a storage hierarchy, and one or more input/output (I/O) devices. In this case, the computer system 102 can execute the treatment program 104, which can be stored in the storage hierarchy in order to implement a process for treating the fluid as described herein. However, it is understood that the computer system 102 can comprise any type of computing device, which may or may not utilize program code, in order to implement a process for treating the fluid as described herein. Furthermore, it is understood that the computer system 102 can include more than one computing device, each of which can perform a portion of a process for treating the fluid as described herein.

The computer system 102 can include one or more I/O devices for interacting with one or more components of the fluid source 110 and/or the fluid destination 116. For example, the computer system 102 can operate a pump, a valve, and/or the like, which controls the flow of the fluid from the fluid source 110 to the filtering component 112 and/or from the ultraviolet component 114 to the fluid destination 116. The computer system 102 can manage the flow control to slow/speed the flow of the fluid, to stop/start the flow of the fluid, route the flow of the fluid, and/or the like. The computer system 102 can perform the flow control in response to a determined level of contamination in the fluid, a determination of one or more malfunctioning components, a target amount of fluid to be treated (e.g., as provided by a user 106), and/or the like.

As discussed herein, the fluid can pass through the filtering component 112, where target contaminants are removed from the fluid, prior to entering the ultraviolet component 114, where the fluid is irradiated by ultraviolet radiation to harm microorganisms that may be present in the fluid using a chamber described herein. The computer system 102 can obtain data corresponding to a contamination level of the fluid from a set of sensors located adjacent to or within the ultraviolet component 114. For example, the computer system 102 can receive data from a sensor located prior to the fluid entering the ultraviolet component 114. Similarly, the computer system 102 can receive data from one or more sensors located within the ultraviolet component 114 (e.g., within the disinfection chamber) and/or one or more sensors located as the fluid is exiting the ultraviolet component 114 (e.g., within the outlet) as described herein. In any event, the computer system 102 can utilize the data acquired by the sensor(s) to determine a level of contamination of the fluid at the given location, confirm that various components, such as the ultraviolet radiation source(s), and/or the like, are properly functioning, adjust operation of one or more of the components, and/or the like. The computer system 102 can use the information, such as the level of contamination, to determine a target amount of ultraviolet radiation to use in treating the fluid to reduce the level of contamination, if necessary, to a level at or below a target level of contamination (e.g., as provided by a user 106).

The computer system 102 can operate the set of UV radiation sources in the ultraviolet component 114 in a manner configured to further improve germicidal efficiency of the ultraviolet irradiation. For example, the computer system 102 can pulse the set of UV radiation sources rather than continuously operating the UV radiation sources. The computer system 102 can implement a pulsing solution configured to provide for a quasi-continuous UV flux at a target level within the contamination chamber while keeping the total power consumption of the system 100 below a target level. Furthermore, when the set of UV radiation sources includes UV radiation sources having a plurality of distinct peak wavelengths, the computer system 102 can implement a pulsing solution configured to maintain the quasi-continuous UV flux for each of the plurality of distinct peak wavelengths. While a single filtering component 112 and single ultraviolet component 114 are shown between the fluid source 110 and the fluid destination 116, it is understood that any number of filtering components 112 and ultraviolet components 114 can be located along the fluid flow path between the fluid source 110 and the fluid destination 116.

While primarily shown and described herein as a chamber configured to increase a level of intensity in an enclosure, it is understood that aspects of the invention further provide various alternative embodiments. For example, in one embodiment, the invention provides a method of fabricating the chamber. In this case, the method can include obtaining a material to be utilized in forming the chamber wall(s) and forming cavities described herein in the material. The material can be selected to have a target refractive index for the radiation to be used during an application of the chamber. The cavities can be formed using any solution, such as cutting or otherwise extracting portions of the material, e.g., using a laser scribing process or the like. Alternatively, the cavities can be formed by molding a transparent polymer (e.g., an ultraviolet transparent polymer), such as a fluoropolymer (e.g., polytetrafluoroethylene (PTFE), a terpolymer of ethylene, tetrafluoroethylene, and hexafluoropropylene (e.g., EFEP offered by Daikin America, Inc.), fluorinated ethylene-propylene (FEP), and/or the like). Furthermore, the formation can include depositing a transparent polymer film on the external and/or internal surfaces of a tube of highly transparent material (e.g., fused silica or sapphire) and subsequently forming grooves in the polymer film. The wall(s) can be configured to form the enclosure and any additional components, if desired, can be added to the chamber (e.g., light source(s), reflective material, absorbing material, and/or the like) using any solution. Subsequently, the chamber can be configured for integration and/or integrated into a system using any solution.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A chamber comprising:
an enclosure configured to trap target radiation therein, wherein the enclosure is at least partially formed by a set of transparent walls having outer and inner surfaces, wherein each transparent wall comprises a first material transparent to the target radiation and having a refractive index greater than 1.1 for the target radiation, wherein a medium located adjacent to the outer surface of the set of transparent walls has a refractive index within approximately one percent of a refractive index of a vacuum for the target radiation, and wherein the outer surface of the set of transparent walls includes a set of cavities, each cavity comprising an approximately prismatic void configured to trap the target radiation within the enclosure by total internal reflection, and wherein the inner surface of at least one transparent wall in the set of transparent walls includes an uneven surface formed by a plurality of side walls, wherein at least one side wall of the plurality of side walls includes a coating of a reflective material and is adjoined by at least two side walls of the plurality of side walls without any coating.

2. The chamber of claim 1, wherein the enclosure comprises a body of revolution.

3. The chamber of claim 1, further comprising an outer container at least partially formed by a set of container walls, wherein the enclosure is located within the outer container.

4. The chamber of claim 3, wherein the set of container walls are formed of at least one of: a reflective material having a reflectivity of at least seventy percent for the target radiation or an absorbing material configured to absorb the target radiation.

5. The chamber of claim 1, wherein each cavity comprises a triangular prism.

6. The chamber of claim 5, wherein two sides of the triangular prism are formed by the outer surface of the set of transparent walls and are orthogonal to each other.

7. The chamber of claim 1, wherein the set of transparent walls are formed of at least one of: sapphire or fused silica.

8. The chamber of claim 1, wherein the uneven surface of the inner surface forms a second set of cavities, and wherein the first and second sets of cavities are aligned to substantially match and are configured to cooperatively trap the target radiation within the enclosure by total internal reflection.

9. The chamber of claim 1, wherein the set of transparent walls forms a torus.

10. The chamber of claim 1, further comprising a light source located within the enclosure, wherein the light source is configured to emit the target radiation.

11. The chamber of claim 10, wherein the light source is configured to emit radiation having a wavelength in a range between approximately 230 nanometers and approximately 360 nanometers.

12. The chamber of claim 10, wherein the light source comprises a mercury lamp located in a central portion of the enclosure.

13. The chamber of claim 10, further comprising a light scattering center located in a central portion of the enclosure, wherein the light source is located adjacent to a wall forming the enclosure and is configured to direct at least partially collimated radiation toward the light scattering center, and wherein the light scattering center includes roughened surfaces.

14. A system comprising:
an enclosure having an inlet for receiving a fluid, wherein the enclosure is configured to trap target radiation therein, wherein the enclosure is at least partially formed by a set of transparent walls having outer and inner surfaces, wherein each transparent wall comprises a first material transparent to the target radiation and having a refractive index greater than 1.1 for the target radiation, wherein a medium located adjacent to the outer surface of the set of transparent walls has a refractive index within approximately one percent of a refractive index of a vacuum for the target radiation, wherein the outer surface of the set of transparent walls includes a set of cavities, each cavity comprising an approximately prismatic void configured to trap the target radiation within the enclosure by total internal reflection, and wherein the inner surface of at least one transparent wall in the set of transparent walls includes an uneven surface formed by a plurality of side walls, wherein at least one side wall of the plurality of side walls includes a coating of a reflective material and is adjoined by at least two side walls of the plurality of side walls without any coating;
a non-emitting light scattering structure located in a central portion of the enclosure extending axially from a first end of the enclosure to an opposing second end, wherein the fluid is located between the light scattering structure and the set of transparent walls of the enclosure; and a plurality of light sources located along at least one side edge of the enclosure radial to the central portion of the enclosure containing the non-emitting light scattering structure, wherein the plurality of light sources are configured to emit at least partially collimated target radiation directed toward the light scattering structure within the enclosure while the fluid is present in the enclosure.

15. The system of claim 14, wherein the target radiation is configured to disinfect the fluid.

16. The system of claim 14, wherein the target radiation is configured to detect a presence of a gas in the fluid.

17. The system of claim 14, further comprising a fluid source fluidly attached to the inlet of the enclosure, wherein the fluid source introduces the fluid into the enclosure using the inlet.

18. A system comprising:
an enclosure having an inlet for receiving a fluid, wherein the enclosure is configured to trap target radiation therein, wherein the enclosure is at least partially formed by a set of transparent walls having outer and inner surfaces, wherein each transparent wall comprises one of: sapphire or fused silica, wherein a medium located adjacent to the outer surface of the set of transparent walls has a refractive index within approximately one percent of a refractive index of a vacuum for ultraviolet radiation, wherein each of the outer and inner surfaces of the set of transparent walls includes a set of cavities, each cavity comprising an approximately prismatic void configured to trap the target radiation within the enclosure by total internal reflection, and wherein an angle of a first prismatic void located on the inner surface and an angle of a second prismatic void located on the outer surface are such that an angle between a ray within the transparent wall and a normal of the outer surface is greater than the total internal reflection angle, and wherein the inner surface of at least one transparent wall in the set of transparent walls includes an uneven surface formed by a plurality of side walls, wherein at least one side wall of the plurality of side walls includes a coating of a reflective material and is adjoined by at least two side walls of the plurality of side walls without any coating; and
a light source located within the enclosure, wherein the light source is configured to emit the ultraviolet radiation within the enclosure while the fluid is present in the enclosure.

19. The system of claim 18, wherein the ultraviolet radiation is configured to disinfect the fluid.

20. The system of claim 18, wherein the light source comprises a mercury lamp located in a central portion of the enclosure.

* * * * *